United States Patent
Dourdeville et al.

(10) Patent No.: US 6,367,847 B1
(45) Date of Patent: Apr. 9, 2002

(54) COUPLER FOR PLACING TWO OR MORE FLUID STREAMS IN COMMUNICATION

(75) Inventors: Theodore A. Dourdeville, Marion; Dennis DellaRovere, Mendon; Joseph D. Antocci, Leominister, all of MA (US)

(73) Assignee: Waters Investments Limited ( * ) Notice: Subject to any disclaimer, the term of this patent is extended or adjusted under 35 U.S.C. 154(b) by 0 days.

(21) Appl. No.: 09/263,453

(22) Filed: Mar. 5, 1999

(51) Int. Cl.[7] ................................................. F16L 39/00
(52) U.S. Cl. ................................ 285/125.1; 285/124.2; 285/FOR 118
(58) Field of Search ............................... 210/198.3, 659; 285/122.1, 124.1, 124.5, FOR 118, 125.1

(56) References Cited

U.S. PATENT DOCUMENTS

| | | | |
|---|---|---|---|
| 2,438,679 A | * | 3/1948 | Parker |
| 4,426,103 A | * | 1/1984 | Sundholm |
| 4,690,437 A | * | 9/1987 | Anderson |
| 4,999,098 A | * | 3/1991 | Pohl et al. |
| 5,132,012 A | * | 7/1992 | Miura et al. |
| 5,658,413 A | * | 8/1997 | Witt et al. |
| 5,888,390 A | * | 3/1999 | Craig |
| 5,935,430 A | * | 8/1999 | Craig |
| 6,033,628 A | * | 3/2000 | Kaltenbach et al. |

FOREIGN PATENT DOCUMENTS

DE            101929    * 3/1899

* cited by examiner

Primary Examiner—Teri Pham Luu
(74) Attorney, Agent, or Firm—Anthony J. Janiuk

(57) ABSTRACT

One embodiment of the present coupler comprises two or more conduits for transporting fluid. Each of the two or more conduits has at least one end defining an opening in said conduit, and each of the conduits has an axis running parallel to the flow of fluid through said conduit. The coupler further comprises a housing body having a first housing planar surface. The housing body holds the two or more conduits in alignment wherein the axis of each conduit is substantially parallel, and at least one end of each conduit is aligned about said first housing planar surface. And, the coupler has a cap element having a cap planar surface. The cap planar surface is fixed to the first housing planar surface in sealed engagement. At least one of the first housing planar surface and the cap planar surface has a channel in fluid communication with the opening in the conduits. The channel allows two or more fluid streams, each fluid stream defined by one of said conduits, to be placed in communication.

22 Claims, 8 Drawing Sheets

COUPLER FOR PLACING TWO OR MORE FLUID STREAMS IN COMMUNICATION

FIELD OF INVENTION

The present invention relates to a coupler for placing two or more fluid streams in communication, and, in particular, capillary scale fluid streams. Embodiments of the present invention provide a coupler for combining or interfacing two or more fluid streams in which one or more fluid streams entering or leaving the coupler has a flow rate of 1 to 200 nanoliters per minute and one or more fluid streams has a flow rate of approximately a 1 to 200 microliters per minute.

BACKGROUND OF THE INVENTION

Analytical instruments often have several fluid streams, which fluid streams carry solutions to or from chromatography columns, pumps, valves, detector assemblies and the like. It is desirable to work with small volumes and to incorporate cleanly flushed geometries. It is sometimes necessary to split a small fluid stream from a larger fluid stream. Conventional fittings and coupling devices have large and often poorly swept internal volumes which may alter or compromise the results obtained when these devices are used.

A coupler for combining and or interfacing two or more fluid streams, where each stream is defined by a conduit, characterized by small internal volume is desired.

SUMMARY OF THE INVENTION

The present invention relates to coupler for placing two or more fluid streams in communication, and, in particular, capillary scale fluid streams. Embodiments of the present invention provide a coupler for combining two and, preferably, three or more fluid streams in which one or more fluid streams has a flow rate of 1 to 200 nanoliters per minute and one or more fluid streams has a flow rate of approximately 1 to 200 microliters per minute.

One embodiment of the present coupler comprises two or more conduits for transporting fluid. Each of the two or more conduits has at least one end defining an opening in said conduit, and each of the conduits has an axis running parallel to the flow of fluid through said conduit. The coupler further comprises a housing body having a first housing planar surface. The housing body holds the two or more conduits in alignment wherein conduits intersect the first housing planar surface. The axes of the conduits are substantially parallel, and at least one end of each conduit is aligned about said first housing planar surface. And, the coupler has a cap element having a cap planar surface. The cap planar surface is fixed to the first housing planar surface in sealed engagement. At least one of the first housing planar surface and the cap planar surface has a channel in fluid communication with the opening in the conduits. The channel allows two or more fluid streams, each fluid stream defined by one of said conduits, to be placed in communication.

Preferably, the coupler combines at least three fluid streams and these streams are defined by the conduits. These conduits are, preferably, fused silica capillary tubes. Fused capillary tubes typically have an outside diameter of 375 microns. Such tubes typically are available with selected internal diameters of 5 to 250 microns. Common tube internal diameters for the present invention comprise internal diameter of approximately 25 microns for 1–200 nanoliters per minute flow rates and approximately 50 microns for 1–200 microliters per minute flow rates.

Preferably, the housing body is an over-molded material such as a plastic. Preferred plastic materials are PEEK and/or PPS. The housing body of over molded plastic can accommodate fused silica tubes of different internal diameters to create fluid streams of different flow rates from a common pressure source. The cap element may be made of the same material or, where electrical contact is desired with the solutions which comprise the fluid streams, a metal or electrically conductive material. A metal cap element allows the fluid to be grounded or an electrical potential imposed on such fluid. Preferably, the ends of each conduit aligned about said first housing planar surface form a line and the channel is a groove in said first housing planar surface. This groove can readily be made by laser etching.

Preferably, the coupler further comprises a clamping assembly holding the first housing planar surface and the cap planar surface in sealed engagement. One preferred clamping assembly comprises one or more screws having threads engaging at least one of the cap element and the housing body. Preferably, the clamp assembly comprises a tab element, and the housing body has a flange for receiving the tab element. Each screw extends through an opening in the cap element and an opening in the tab element. Preferably, at least of the openings of the tab element and the cap element has threads to receive cooperating threads of the screw. The tab element is a circular ring or C-shaped ring.

A further preferred clamp assembly comprises a tab element, and a cap retaining element. The housing body has a housing flange for receiving the tab element. And, the cap element has an cap flange for engaging the cap retaining element. At least one of the cap element and tab element has an opening for receiving the other, and said cap element and tab element having cooperating thread surfaces. The cap element and tab element are joined by the opening for receiving the other with the cooperating threads.

Preferably, such clamp assembly comprises bearing means interposed between at least one of the group consisting of said tab element and cap element, on one hand, and the clamping element, on the other. The bearing means allows at least on of the cap element and tab element to rotate with respect to the clamp element.

Preferably, the housing body and the cap element have alignment elements.

A further embodiment of the present invention comprises a coupler for placing two or more fluid streams in communication. Such coupler comprises two or more conduits for transporting fluid. Each of the two or more conduits has at least one end defining an opening in the conduit. Each of the conduits has an axis running parallel to the flow of fluid through the conduit. The coupler further comprises a first housing body having a first housing planar surface. The first housing body holds one or more conduits in alignment wherein the axis of each conduit is substantially parallel, and at least one end of each conduit is aligned about the first housing planar surface. The coupler further comprises a second housing body having a second housing planar surface. The second housing body holds one or more conduits in alignment wherein the axis of each conduit is substantially parallel, and at least one end of each conduit is aligned about the second housing planar surface. The second housing planar surface is fixed to said first housing planar surface in sealed engagement with at least one of the conduits of the first housing body and the second housing body in fluid communication. The first and second housing bodies allow two or more fluid streams, each fluid stream defined by one of said conduits, to be placed in communication.

Preferably, at least one of the first housing body and the second housing body has two or more conduits. The two or more conduits are held in alignment wherein the axes of the conduits are substantially parallel, and at least one end of each conduit is aligned about the first housing planar surface. At least one of the first housing planar surface and the second housing planar surface has a channel in fluid communication with the openings in the two or more conduits. The channel allows three fluid streams, each fluid stream defined by one of said conduits, to be placed in communication.

Again, the conduits are, preferably, fused silica capillary tubes. Fused capillary tubes typically have an outside diameter of 375 microns. Such tubes typically are available with selected internal diameters of 5 to 250 microns. Common tube internal diameter sizes for the present invention comprise internal diameter tubes of approximately 25 microns for 1–200 nanoliters per minute flow rates and approximately 50 microns for 1–200 microliters per minute flow rates.

Preferably, the housing body is an over-molded material such as plastic. Preferred plastic materials are PEEK and/or PPS. The housing body of over molded plastic can accommodate fused silica tubes of different internal diameters to create fluid streams of different flow rates.

Preferably, the channel is a groove in said first housing planar surface.

Preferably, the coupler further comprises a clamping assembly holding the first housing planar surface and the second housing planar surface in sealed engagement.

A further embodiment of the present invention comprises a method for making a coupler for placing two or more fluid streams in communication. The method comprises the steps of providing two or more conduits for transporting fluid. Each of the two or more conduits has at least one end defining opening in the conduits. Each of the conduits has an axis running parallel to the flow of fluid through the conduit. The method further comprises the step of providing a housing body having a first housing planar surface. The first housing body holds one or more conduits in alignment wherein the axes of the conduits are substantially parallel, and at least one end of each conduit is aligned about the first housing planar surface. The method further comprises providing a cap element having a cap planar surface where the first housing body has two or more conduits. The cap element is fixed to said first housing planar surface in sealed engagement. In the alternative, the method comprises the step of providing a second housing body having a second housing planar surface. The second housing body holds one or more conduits in alignment wherein the axis of each conduit is substantially parallel, and at least one end of each conduit is aligned about the second housing planar surface. Where one of the first housing body or the second housing body has two or more conduits, at least one of the first housing planar surface, second housing planar surface and said cap planar surface has a channel in fluid communication with the openings in the two or more conduits. The channel allows two or more fluid streams, each fluid stream defined by one of said conduits, to be placed in communication.

Preferably, the housing body is comprised of an over-molded material which material is potted or molded about said conduits. A preferred over molded material is plastic. A preferred plastic is PEEK and/or PPS. The method has particular application where the conduits are fused silica capillary tubes. After the housing body is formed, the excess fused silica capillary tubes are trimmed flat with the planar surfaces. A groove forming a channel may be mechanically carved into the planar surface or laser etched.

These and other features and advantages will be apparent to those skilled in the art from an examination of the figures and a reading of the detailed description which follows.

DETAILED DESCRIPTION OF THE INVENTION

The present invention relates to coupler for placing two or more fluid streams in communication, and, in particular, capillary scale fluid streams. Embodiments of the present invention provide a coupler for combining or interfacing two and, preferably, three or more fluid streams in which one or more fluid streams has a flow rate of 1 to 200 nanoliters per minute and one or more fluid streams has a flow rate of approximately 1 to 200 microliters per minute. Embodiments of the present invention have particular applications in transporting micro-volumes of fluids. These embodiments are particularly useful in coupling disparate analytical apparatus to fluid streams originating with high performance liquid chromatography. For example, the couplers described herein can be used to place mass spectrometry apparatus in fluid communication with chromatography devices.

Figure 1:
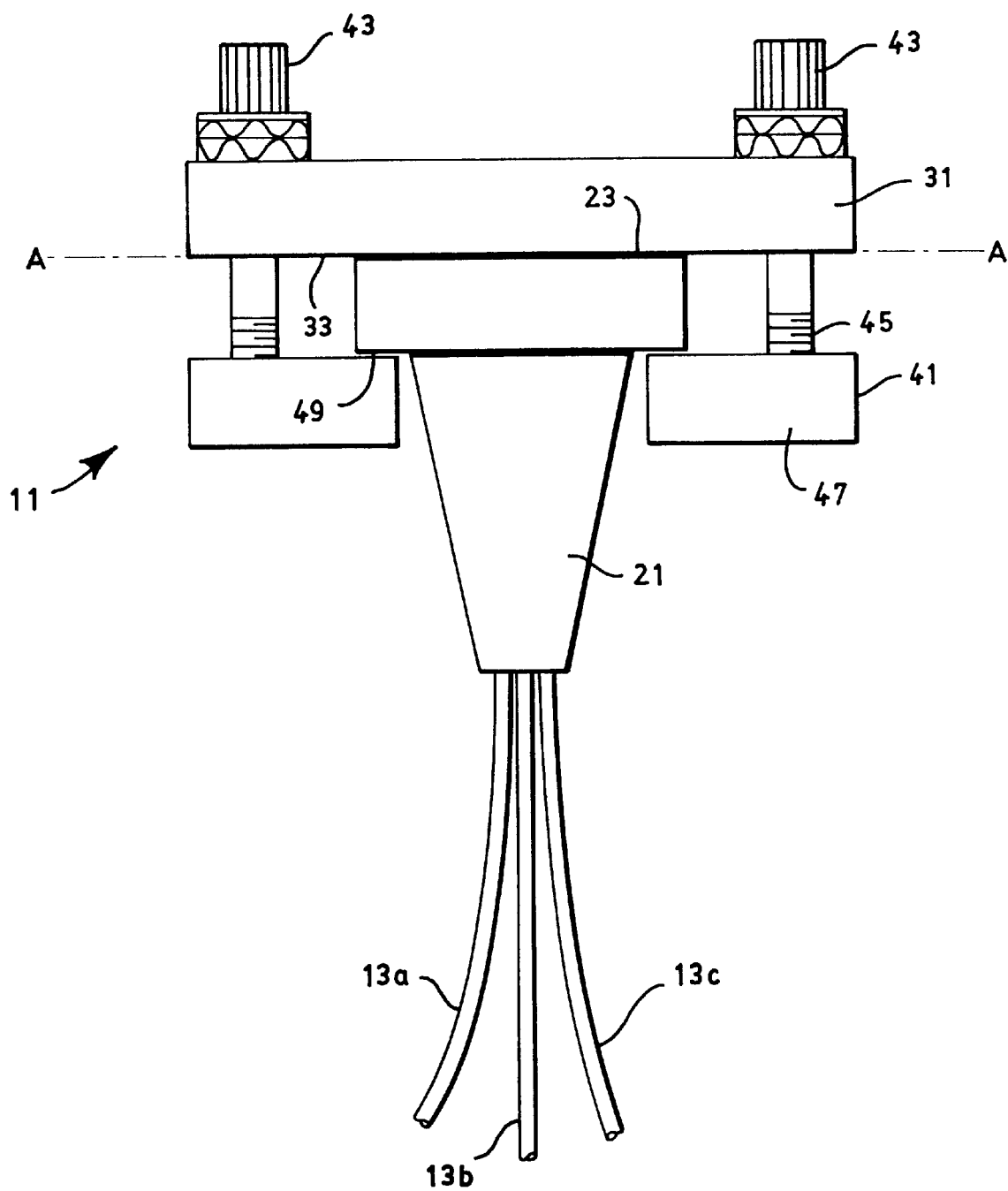
FIG. 1 depicts a side partially sectional view of one embodiment of the present invention.
Figure 2:
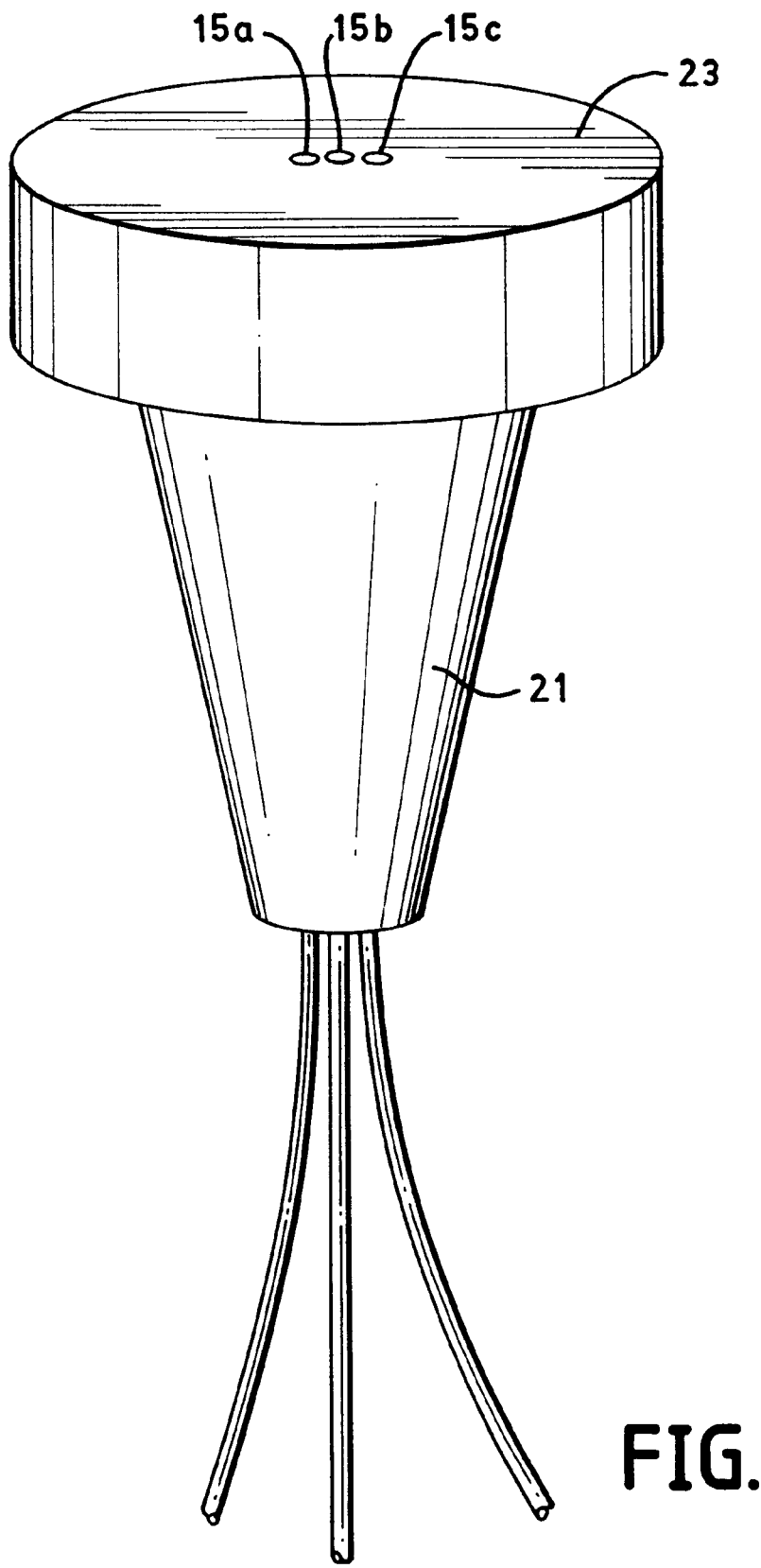
FIG. 2 depicts a slightly elevated, partially sectional view of a housing body embodying features of the present invention.

Turning now to FIG. 1, one embodiment of the present coupler, generally designated by the numeral 11, has three conduits 13a, 13b, and 13c for transporting fluid. Each of the conduits 13a, 13b, and 13c has at least one end 15a, 15b and 15c, as best seen in FIG. 2, defining an opening in the conduit. Each of the conduits 13a, 13b, and 13c has an axis running parallel to the flow of fluid through the conduit.

The coupler 11 further comprises a housing body 21 having a first housing planar surface 23. The housing body 21 is frusto-conical in shape tapering at the end opposite the planar surface 23. The housing body holds conduits 13a, 13b, and 13c in alignment wherein the axis of each conduit is substantially parallel to each other, and at least one end of each conduit 15a, 15b, and 15c is aligned about said first housing planar surface 23.

Figure 3:
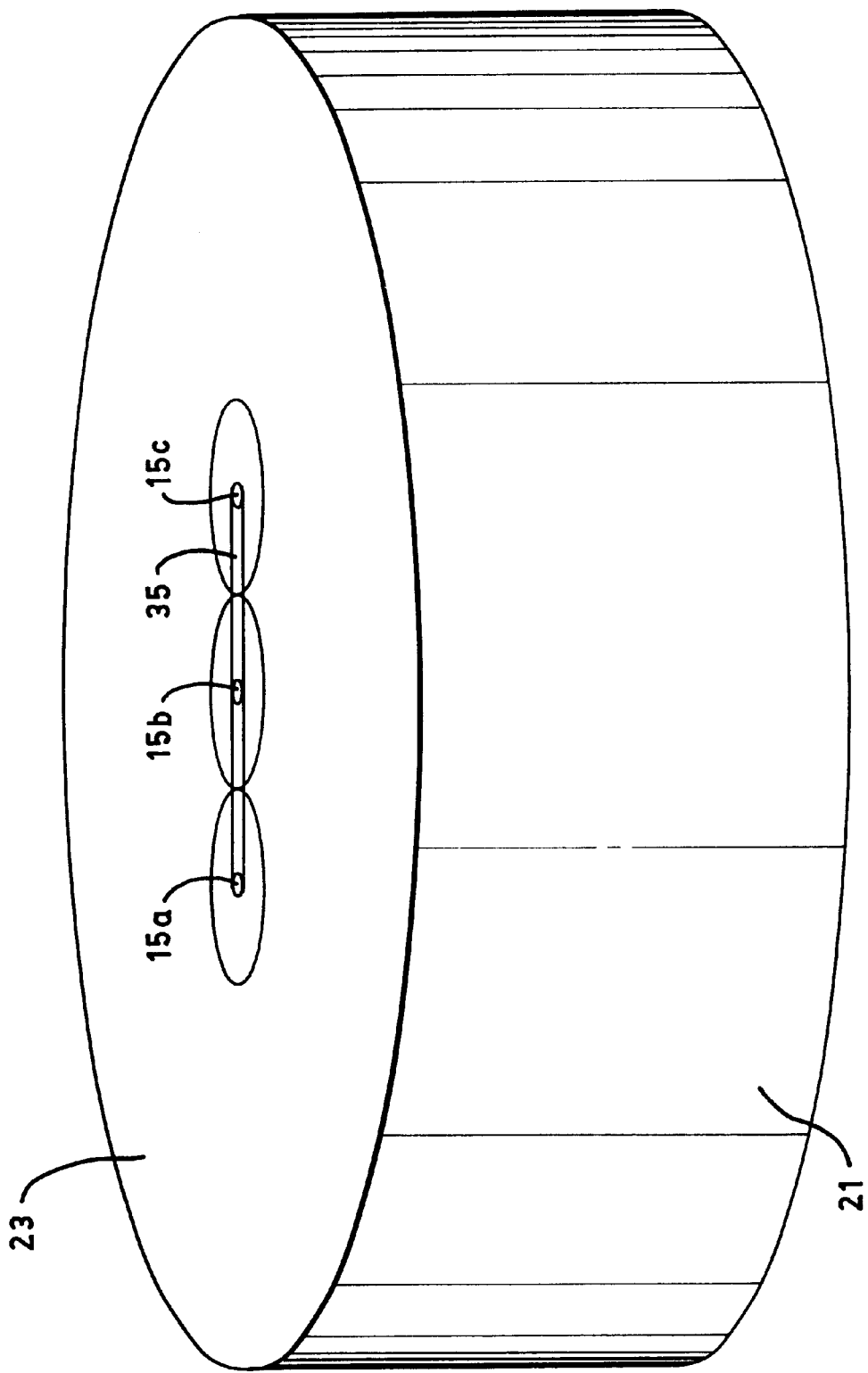
FIG. 3 depicts a slightly elevated view of a first housing planar surface embodying features of the present invention.

Coupler 11 has a cap element 31 having a cap planar surface 33. The cap planar surface 33 is fixed to the first housing planar surface 23 in sealed engagement. At least one of the first housing planar surface 23 and the cap planar surface 33 has a channel 35 in fluid communication with the openings 15a, 15b, and 15c in the conduits 13a, 13b, and 13c, as best seen in FIG. 3. FIG. 3 depicts such channel 35 in the housing body 21. The channel 35 allows two or more fluid streams, each fluid stream defined by one of said conduits 13a, 13b, and 13c to be placed in communication.

Conduits 13a, 13b, and 13c are, preferably, fused silica capillary tubes. Fused silica capillary tubes typically have an outside diameter of 375 microns. Such tubes typically are available with selected internal diameters of 5 to 250 microns. Common tube internal diameters for the present invention comprise internal diameter tubes of approximately 25 microns for 1–200 nanoliters per minute flow rates and approximately 50 microns for 1–200 microliters per minute flow rates.

Preferably, the housing body 21 is an over-molded material such as a plastic. Preferred plastic materials are PEEK and/or PPS. The housing body 21, of over molded plastic, can accommodate fused silica tubes of different internal diameters to create fluid streams of different flow rates. The cap element 31 may be made of the same material or, where electrical contact is desired with the solutions which comprise the fluid streams, a metal or electrically conductive material. A metal cap element allows the fluid to be grounded or an electrical potential imposed on such fluid.

Preferably, the ends 15a, 15b and 15c of each conduit 13a, 13b, and 13c, aligned about said first housing planar surface 23, form a line and the channel 35 is a groove in said first housing planar surface 23. This groove can readily be made by laser etching.

As illustrated in FIG. 1, the coupler 11 further comprises a clamp assembly 41 holding the first housing planar surface 23 and the cap planar surface 33 in sealed engagement. Clamp assembly 41 has two screws 43 and a tab element 47. Screws 43 have threads 45 engaging at least one of the cap element 31, the housing body 21 or tab element 47. The housing body 21 has a flange 49 for receiving the tab element 47. Each screw extends through an opening (not shown) in the cap element 31 and an opening (not shown) in the tab element 47. Preferably, at least one of the openings of the tab element 47 and the cap element 31 has threads to receive cooperating threads 45 of the screw 43. The tab element 47 is a circular ring or C-shaped ring.

Figure 4:
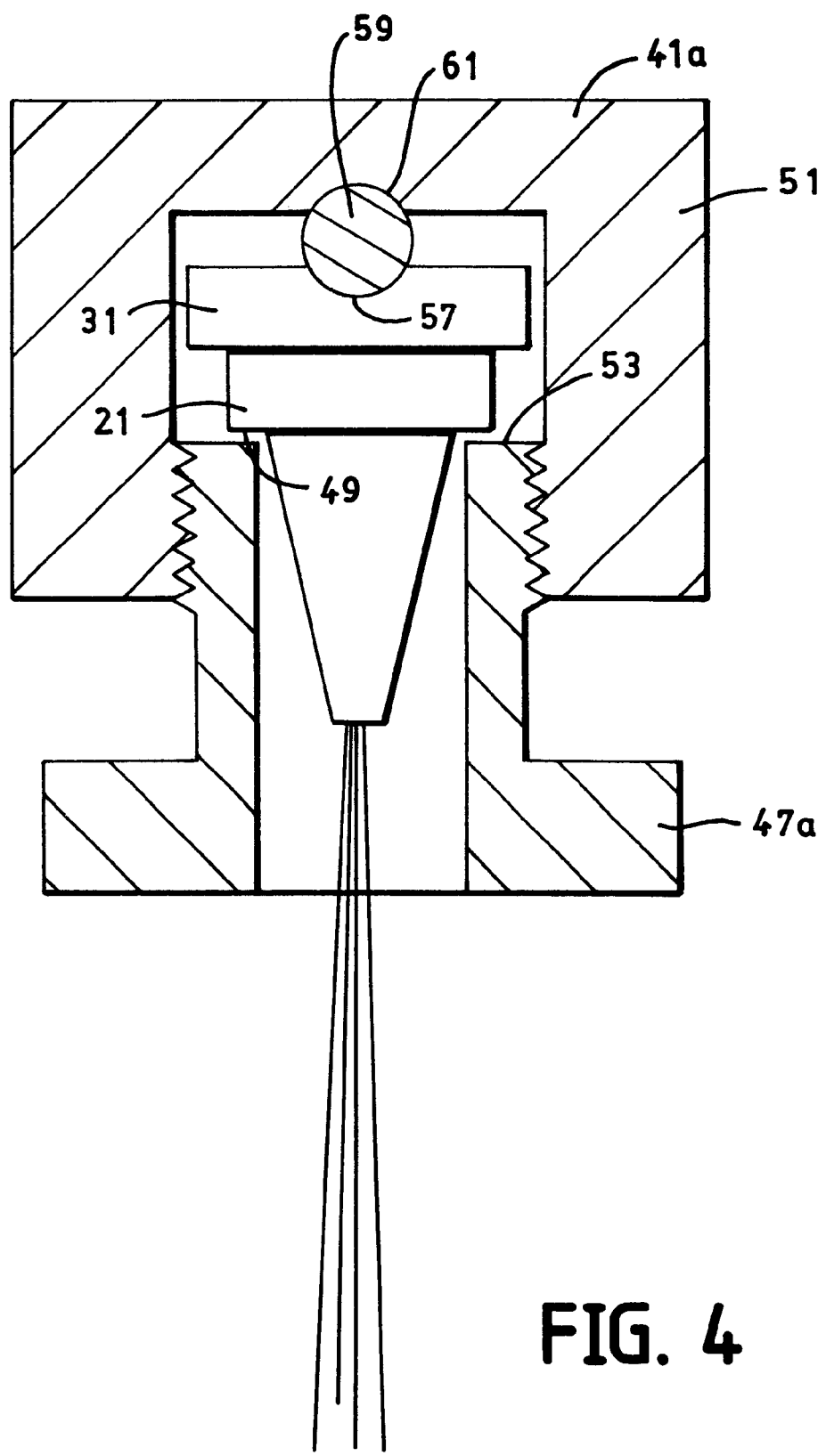
FIG. 4 depicts a side, partially sectional view of a further embodiment of the present invention.

Turning now to FIG. 4, a further clamp assembly 41a is depicted. Clamp assembly 41a comprises a tab element 47a, and a cap retaining element 51. The housing body 21 has a housing flange 49 for receiving the tab element 47a on an abutment edge 53. Cap element 31 has a cap flange for engaging the cap retaining element 51 or some other engaging surface. As illustrated, cap element 31 has an indentation 57 for receiving a bearing 59. Similarly, cap retaining element 51 has an indentation 61. The bearing 59 allows at least on of the cap element 31 and tab element 47a to rotate with respect to the cap retaining element 51. The cap retaining element 51 has an opening for receiving the cap element 31, housing body 21 and tab element 47a. The cap retaining element 51 and tab element 47a having cooperating thread surfaces. The cap retaining element 51 and tab element 47a are joined with the cooperating threads.

Figure 5:
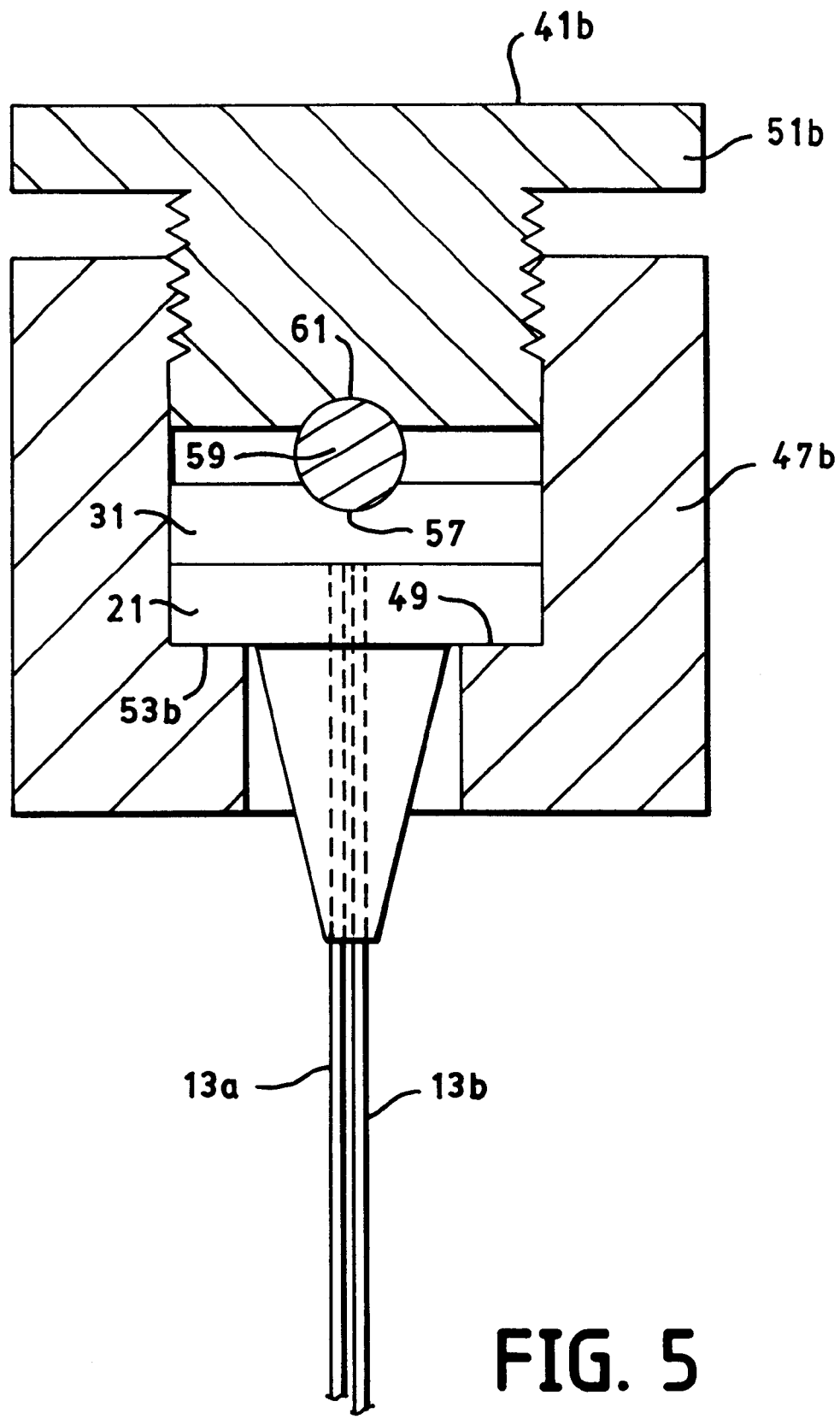
FIG. 5 depicts a side, partially sectional view of a further embodiment of the present invention.

Turning now to FIG. 5, a further clamp assembly 41b is depicted. Clamp assembly 41b comprises a tab element 47b, and a cap retaining element 51b. The housing body 21 has a housing flange 49 for receiving the tab element 47b on an abutment edge 53b. Cap element 31 has a cap flange for engaging the cap retaining element 51b or some other engaging surface. As illustrated, cap element 31 has an indentation 57 for receiving a bearing 59. Similarly, cap retaining element 51b has an indentation 61. The bearing 59 allows at least on of the cap element 31 and tab element 47b to rotate with respect to the cap retaining element 51b. The tab element 47b has an opening for receiving the cap retaining element 51b, cap element 31, housing body 21. The cap retaining element 51b and tab element 47b having cooperating thread surfaces. The cap retaining element 51b and tab element 47b are joined with the cooperating threads.

Figure 6:
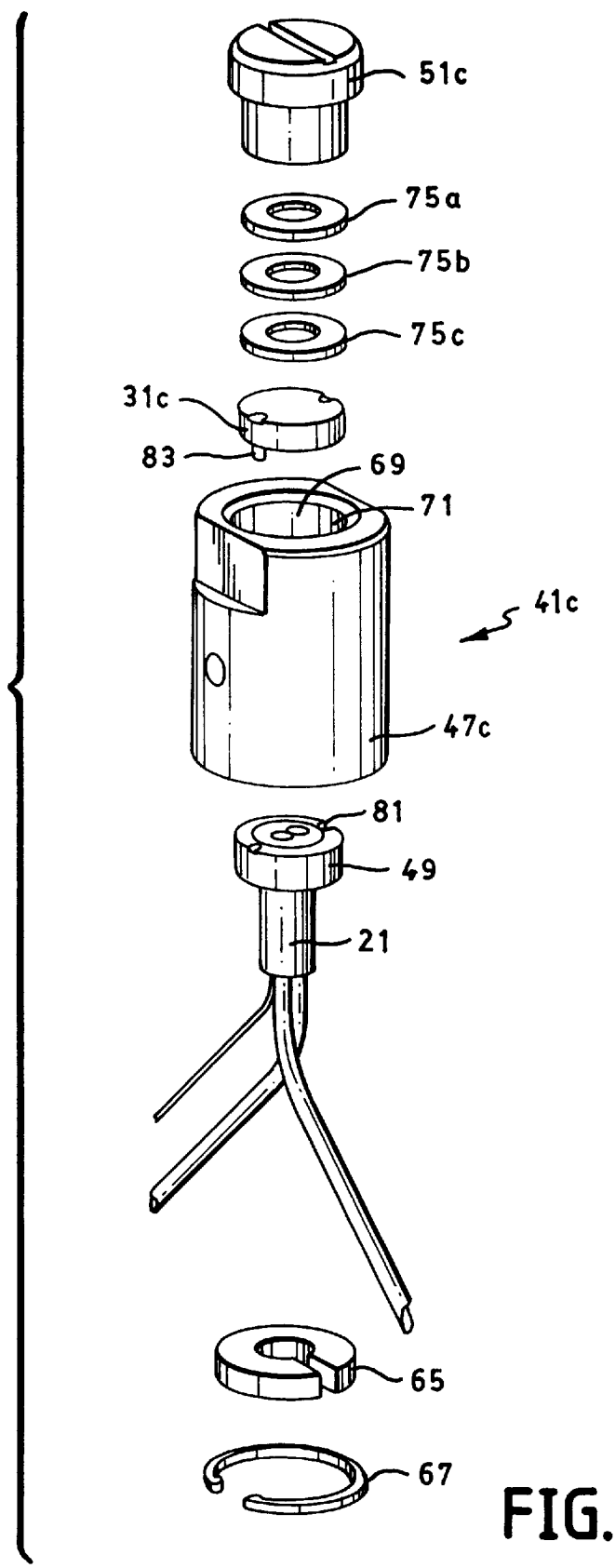
FIG. 6 depicts a side, exploded view of a further embodiment of the present invention.
Figure 7:
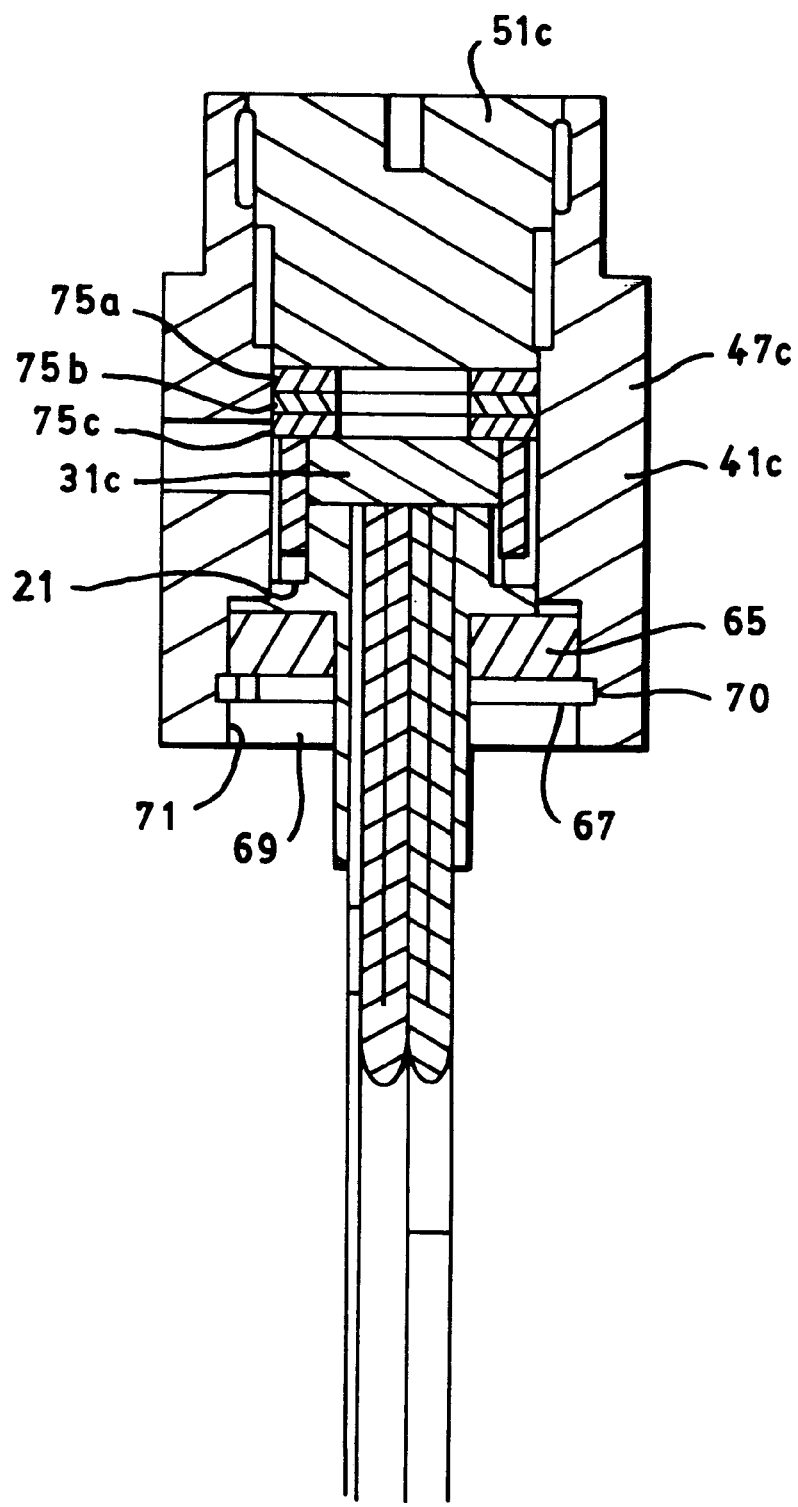
FIG. 7 depicts a side view of a embodiment of the present invention of FIG. 6; and, FIG. 8 depicts a side, partially sectional view of a further embodiment of the present invention.

Turning now to FIGS. 6 and 7, a further clamp assembly 41c is depicted. Clamp assembly 41c is similar to that described with respect to FIG. 5. Clamp assembly 41c comprises a tab element 47c, and a cap retaining element 51c. Tab element 41c is an open cylinder having an inner wall 71 defining an opening 69. Tab element 41c further comprises an abutment C-ring 65 and a retaining clip 67. Abutment ring 65 is received within an opening 69. Retaining clip 67 is flexible and is received in a indentation 73 to allow removal of the retaining clip 67 if necessary. Retaining clip 67 holds abutment C-ring 65 in the tab element 41c. The housing body 21 has a housing flange 49 for receiving the abutment C-ring 65.

Cap element 31 has an engaging surface along the upper edge surface for receiving three ring bearings 75a, 75b, and 75c. The ring bearings 75a, 75b, and 75c 59 allow at least on of the cap element 31 and tab element 47c to rotate with respect to the cap retaining element 51c. The tab element 47c has an opening 69 for receiving the cap retaining element 51c, cap element 31c, and housing body 21. The cap retaining element 51c and tab element 47c having cooperating thread surfaces (not shown) or some other retaining system. The cap retaining element 51c and tab element 47c are joined with the cooperating threads or such other retaining system.

Preferably, the housing body 21 and the cap element 31 have alignment elements illustrated as interfitting pins and holes 81 and 83 as best seen in FIG. 6.

Figure 8:
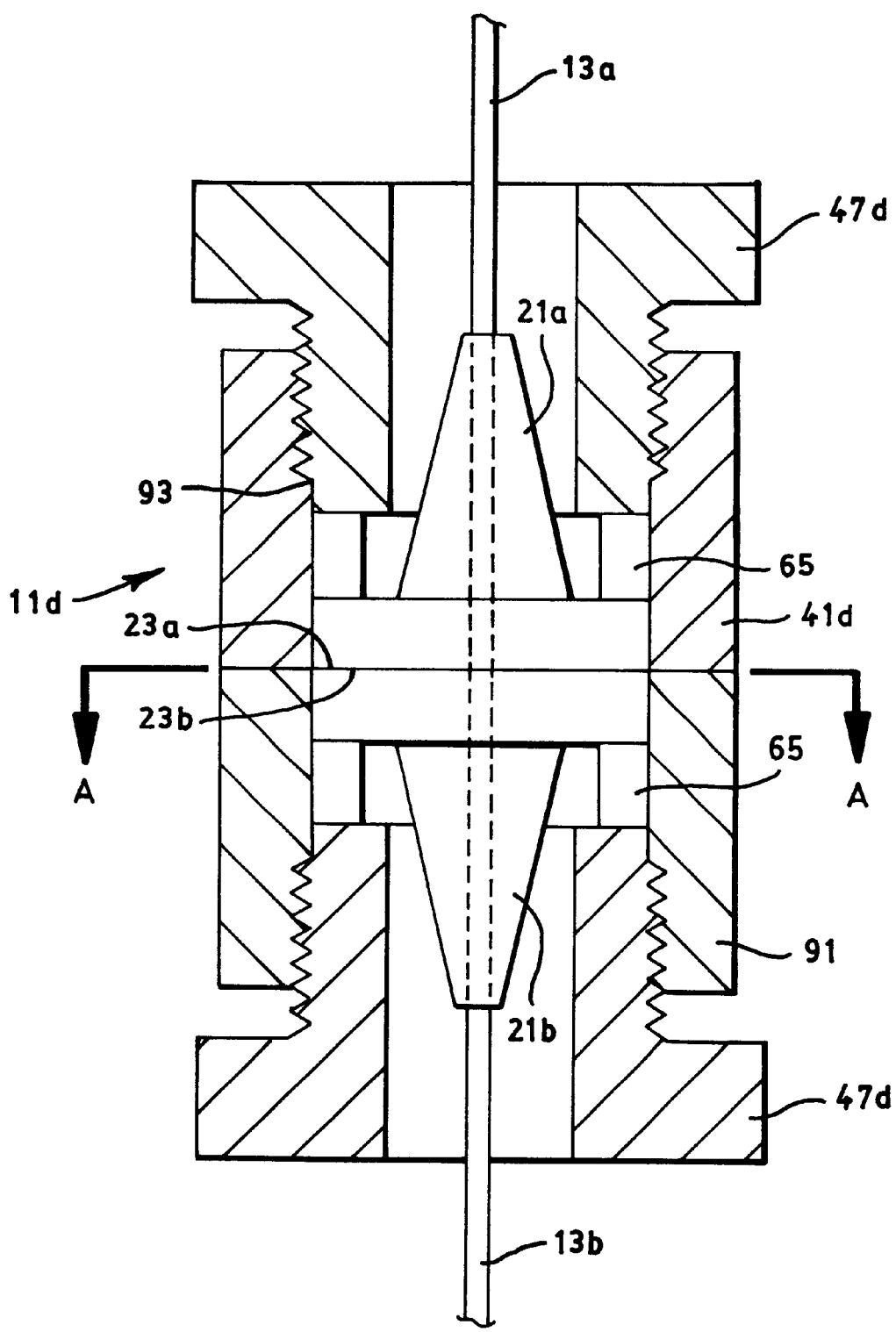

A further embodiment of the present invention comprises a coupler 11d for placing two or more fluid streams in communication, as best seen in FIG. 8. Coupler 11d comprises a first housing body 21a and a second housing body 21b. Each housing body 21a and 21b has a conduit 13a and 13b, respectively, for transporting fluid. Each of the two conduits 13a and 13b has at least one end (not shown) defining an opening in the conduit. Each of the conduits 13a and 13b has an axis running parallel to the flow of fluid through the conduit. First housing body 21a having a first housing planar surface 23a. First housing body 21a holds conduit 13a in alignment wherein the axis of the conduit is substantially perpendicular to, and the opening is aligned about the first housing planar surface 23a.

Second housing body 21b has a second housing planar surface 23b. The second housing body 21b holds conduit 13b in alignment wherein the axis of each conduit is substantially perpendicular to, and the one end of conduit 13b is aligned with the second housing planar surface 23b. The second housing planar surface 23b is fixed to said first housing planar surface 23a in sealed engagement with conduit 13a of the first housing body 21a and conduit 13b of the second housing body in fluid communication. The first and second housing bodies allow two or more fluid streams, each fluid stream defined by one of said conduits, to be placed in communication. Each housing body 21 a and 21b may hold additional conduits, for example, in the manner of the housing body 21 described in FIG. 2.

A clamp assembly 41d holds first housing body 21a and second housing body 21b with first housing planar surface 23a and second housing planar surface 23b in sealed engagement. Clamp assembly 41 has a cylindrical clamp housing 91 with an interior wall 93. First housing body 21a and second housing body 21b are held in the clamp housing 91 by tab elements 47d and abutment C-rings 65. Tab elements 47d and clamp housing 91 have cooperating threads which hold tab elements 47d in place.

A farther embodiment of the present invention comprises a method for making a coupler 11 for placing two or more fluid streams in communication. The method comprises the steps of providing two or more conduits 13a and 13b for transporting fluid. Each of the two or more conduits has at least one end defining opening in the conduits. Each of the conduits has an axis running parallel to the flow of fluid through the conduit. The method further comprises the step of providing a housing body 21 having a first housing planar surface. The first housing body 21 holds at least one conduit 13 in alignment wherein the axis of the conduit is substantially perpendicular to the planar surface 23. And, at least one end of each conduit 13 is aligned about the first housing planar surface 23. The method further comprises providing a cap element 31 having a cap planar surface 33 where the first housing body 21 has two or more conduits. The cap element 31 is fixed to said first housing planar surface 21 in sealed engagement.

In the alternative, the method comprises the step of providing a second housing body 21b having a second housing planar surface 23b. The second housing body 23b holds at least one conduit 13 in alignment wherein the axis of the conduit is substantially perpendicular to the planar surface 23b. And, at least one end of each conduit is aligned about the second housing planar surface 23b.

Where one of the first housing body 21a or the second housing body 21b has two or more conduits, at least one of the first housing planar surface, second housing planar surface and said cap planar surface has a channel in fluid communication with the openings in the two or more conduits. The channel allows two or more fluid streams, each fluid stream defined by one of said conduits, to be placed in communication.

Preferably, the housing body 21 is comprised of an over-molded material which material is potted about said conduits. A preferred over molded material is plastic. A preferred plastic is PEEK and PPS. The method has particular application where the conduits are fused silica capillary tubes. After the housing body is formed, the excess fused silica capillary tubes are trimmed flat with the planar surfaces. A groove forming a channel may be mechanically carved into the planar surface or laser etched.

Thus, the present invention has been described with respect to preferred embodiments with the understanding that the invention is subject to modification and alteration. It is thus understood that the invention should not be so limited but should encompass the subject matter falling within the purview of the following claims.

What is claimed is:

1. A coupler for placing two or more fluid streams in communication, comprising:
   a. two or more conduits for transporting fluid, each of said two or more conduits having at least one end defining an opening in said conduit;
   b. a first housing body having a first planar surface, said first housing body holding said two or more conduits in alignment wherein at least one end of each conduit is aligned about said first housing planar surface;
   c. a cap element having a cap planar surface, said cap fixed to said first housing planar surface in sealed engagement, and at least one of said first housing planar surface and said cap planar surface having a channel in fluid communication with said opening in said conduits, said channel allowing two or more fluid streams, each fluid stream defined by said one of said conduits, to be placed in communication; and,
   d. a clamping assembly holding said first housing planar surface and said cap planar surface in sealed engagement, wherein said clamping assembly comprises a tab element, said tab element comprising a circular ring or c-shaped ring substantially encircling said housing body, said housing body having a flange for receiving said tab element, and said clamping assembly further comprises at least one screw having threads, each screw extending through an opening in said tab element and at least one opening in one of said cap element and housing body having cooperating threads.

2. The coupler of claim 1 wherein said two or more fluid streams comprise at least three fluid streams.

3. The coupler of claim 1 wherein said conduits are fused silica capillary tubes.

4. The coupler of claim 1 wherein said housing body is an over-molded material.

5. The coupler of claim 4 wherein said over-molded material is plastic.

6. The coupler of claim 5 wherein said plastic is PEEK.

7. The coupler of claim 1 wherein said channel is a groove in said first housing planar surface.

8. A coupler for placing two or more fluid streams in communication, comprising:
   a. two or more conduits for transporting fluid, each of said two or more conduits having at least one end defining an opening in said conduit;
   b. a first housing body having a first planar surface, said first housing body holding said two or more conduits in alignment wherein at least one end of each conduit is aligned about said first housing planar surface;
   c. a cap element having a cap planar surface, said cap fixed to said first housing planar surface in sealed engagement, and at least one of said first housing planar surface and said cap planar surface having a channel in fluid communication with said opening in said conduits, said channel allowing two or more fluid streams, each fluid stream defined by said one of said conduits, to be placed in communication; and,
   d. a clamping assembly holding said first housing planar surface and said cap planar surface in sealed engagement said clamp assembly comprising a tab element, and a cap retaining element, said housing body has a housing flange for receiving said tab element, and said cap element has a cap flange for engaging said cap retaining element, at least one of said cap element and tab element having cooperating thread surfaces, for receiving the other with said cooperating threads to join said two or more conduits at said openings.

9. The coupler of claim 8 further comprising bearing means interposed between at least one of the group consisting of said tab element and cap element, on one hand, and said clamping element, on the other, to allow at least one of said cap element and tab element to engage and rotate with respect to said clamp element through said bearing means.

10. The coupler of claim 8 wherein said housing body and said cap element have alignment elements.

11. A method of making a coupler for placing two or more fluid streams in communication, comprising the following steps:

a. providing two or more conduits for transporting fluid, each of said two or more conduits having at least one end defining an opening in said conduit;

b. providing a first housing body having a first planar surface, said first housing body holding at least one of said two or more conduits in alignment wherein at least one end of each conduit is aligned about said first housing planar surface;

c. providing at least one of the group consisting of a second housing body and a cap element, said second housing body having a second housing body planar surface, said second housing body holding said one or more conduits in alignment wherein at least one end of each conduit is aligned about said second housing planar surface in fluid communication with one or more conduits in said first housing body, said cap element having a cap planar surface, said cap element and said second housing body planar surface fixed to said first housing planar surface in sealed engagement, and, wherein said cap element is provided, at least one of said first housing planar surface and said cap planar surface having a channel in fluid communication with said opening in said conduits, said channel allowing two or more fluid streams, each fluid stream defined by said one of said conduits, to be placed in communication; and, d. providing a clamping assembly holding said first housing planar surface and one of said second housing planar surface and said cap planar surface in sealed engagement.

12. The method of claim 11 wherein said conduits are fused silica capillary tubes.

13. The method of claim 11 wherein said housing body is an over-molded material which material is potted about said conduits.

14. The method of claim 13 wherein said over-molded material is plastic.

15. The method of claim 14 wherein said plastic is PEEK and PPS.

16. A coupler for placing two or more fluid streams in communication, comprising:

a. two or more conduits for transporting fluid, each of said two or more conduits a having at least one end defining an opening is said conduit;

b. a first housing body having a first housing body planar surface, said first housing body holding one or more conduits in alignment wherein at least one end of each conduit is aligned about said first housing planar surface;

c. a second housing body having a second housing body planar surface, said second housing body holding said one or more conduits in alignment wherein at least one end of each conduit is aligned about said second housing planar surface; said second housing planar surface fixed to said first housing planar surface in sealed engagement with at least one of said conduits of said first housing body and said second housing body in fluid communication, allowing two or more fluid streams, each stream defined by one of said conduits, to be placed in communication; and, d. a clamping assembly holding said first housing planar surface and said second housing planar surface in sealed engagement said clamp assembly comprising cylindrical clamp housing, a tab element, and a second housing retaining element, said cylindrical clamp housing having an opening for receiving said first housing body, tab element, second housing body and second housing retaining element, said first housing body has a first housing flange for receiving said tab element, and said second housing element has a second housing flange for engaging said second housing retaining element, said second housing retaining element and tab element held in said clamp housing and at least one of said second housing retaining element and tab element having thread surfaces which cooperate with thread surfaces on said clamp housing, said second housing retaining element and tab element joined by said opening for receiving the other with said cooperating threads.

17. The coupler of claim 16 wherein at least one of said first housing body and said second housing body has two or more conduits, said two or more conduits in alignment wherein at least one end of each conduit is aligned about said first housing planar surface; and at least one of said first housing planar surface and said second housing planar surface having a channel in fluid communication with said openings in said two or more conduits, said channel allowing three fluid streams, each fluid stream defined by one of said conduits, to be placed in communication.

18. The coupler of claim 16 wherein said conduits are fused silica capillary tubes.

19. The coupler of claim 16 wherein said housing body is an over-molded material.

20. The coupler of claim 19 wherein said over-molded material is plastic.

21. The coupler of claim 20 wherein said plastic is PEEK or PPS.

22. The coupler of claim 16 wherein at least one of said first and second housings have more than on conduit, said conduit in communication with at least one other conduit via a channel, wherein said channel is a groove in said first housing planar surface.

* * * * *